(12) United States Patent
Imaizumi

(10) Patent No.: US 7,275,828 B2
(45) Date of Patent: Oct. 2, 2007

(54) EYE REFRACTIVE POWER MEASUREMENT APPARATUS

(75) Inventor: Satoshi Imaizumi, Hoi-gun (JP)

(73) Assignee: Nidek Co., Ltd., Gamagori (JP)

( * ) Notice: Subject to any disclaimer, the term of this patent is extended or adjusted under 35 U.S.C. 154(b) by 275 days.

(21) Appl. No.: 11/188,628

(22) Filed: Jul. 26, 2005

(65) Prior Publication Data

US 2006/0023161 A1 Feb. 2, 2006

(30) Foreign Application Priority Data

Jul. 30, 2004 (JP) ............................ 2004-224719

(51) Int. Cl.
*A61B 3/10* (2006.01)
*A61B 3/14* (2006.01)
(52) U.S. Cl. ...................... 351/212; 351/206
(58) Field of Classification Search ............... 351/205, 351/206, 212
See application file for complete search history.

(56) References Cited

U.S. PATENT DOCUMENTS 5,309,186 A * 5/1994 Mizuno ................... 351/212

6,354,705 B1 3/2002 Hirohara et al.
2005/0068497 A1 3/2005 Hanebuchi et al.

FOREIGN PATENT DOCUMENTS

| JP | A 4-73038 | 3/1992 |
| JP | A 2000-126133 | 5/2000 |
| JP | A 2002-336200 | 11/2002 |

* cited by examiner

*Primary Examiner*—Scott J. Sugarman
(74) *Attorney, Agent, or Firm*—Oliff & Berridge, PLC

(57) ABSTRACT

An eye refractive power measurement apparatus capable of accurate measurement while preventing noise light from entering a photodetector even a measurement target is moved in an optical-axis direction, has a measurement optical system including an optical axis, a hole mirror having an aperture and a reflective surface, a concave mirror, an optical system projecting measurement light from the target onto a fundus via the aperture and the concave mirror, and an optical system having an image-forming member and the photodetector photo-receiving the light reflected from the fundus via the concave mirror, the reflective surface and the image-forming member, a unit moving the target and the image-forming member or photodetector in the direction to have a positional relationship optically conjugate with the fundus, and a calculation part obtaining eye refractive power based on a travel position or amount of the image-forming member or photodetector and an output from the photodetector.

6 Claims, 3 Drawing Sheets

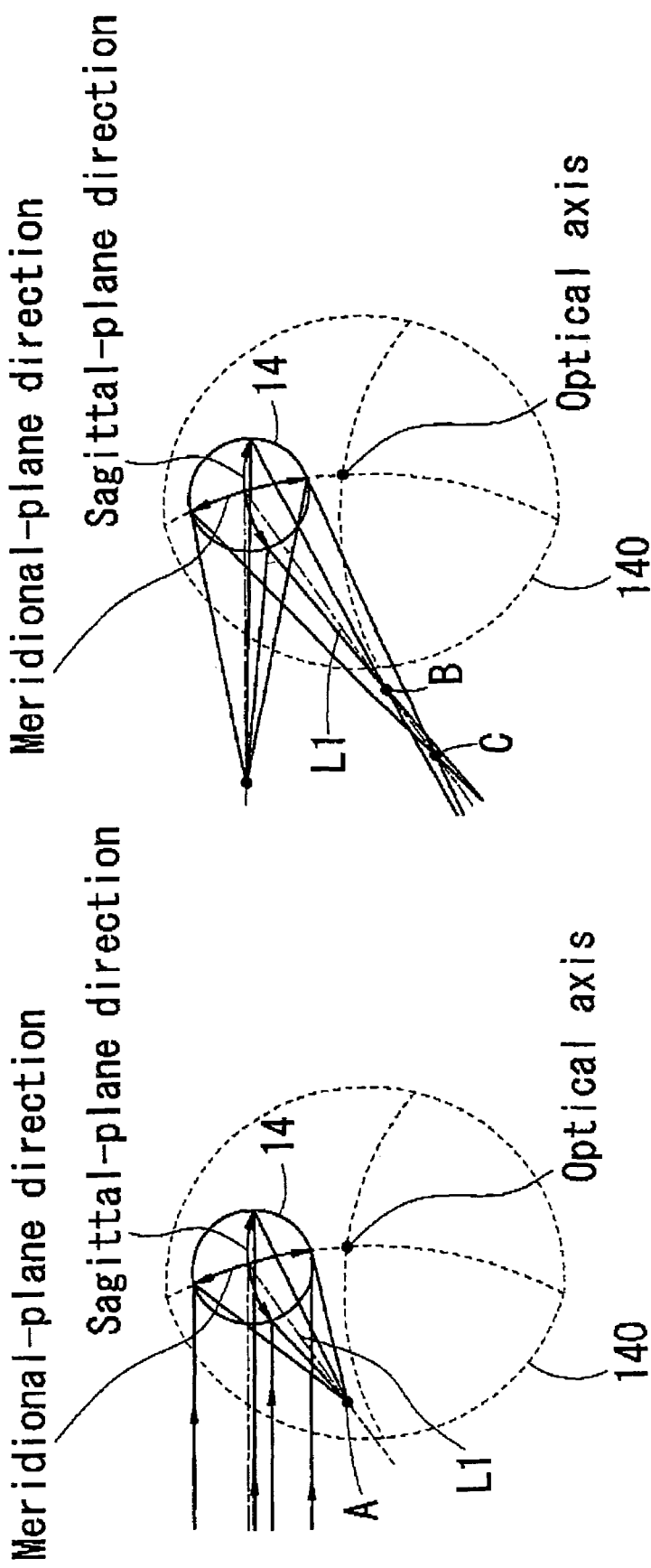

EYE REFRACTIVE POWER MEASUREMENT APPARATUS

BACKGROUND OF THE INVENTION

1. Field of the Invention

The present invention relates to an eye refractive power measurement apparatus for measuring eye refractive power of an eye of an examinee objectively.

2. Description of Related Art

Conventionally, there is known an eye refractive power measurement apparatus having a measurement optical system which includes a projection optical system for projecting measurement light from a measurement target onto a fundus of an eye of an examinee via an objective lens and a photo-receiving optical system for photo-receiving the measurement light reflected from the fundus via the objective lens in the projection optical system by using a photodetector. In such a configuration, the objective lens is shared by the projection optical system and the photo-receiving optical system; therefore, there is such a problem that the measurement light from the measurement target is reflected by the objective lens to inadvertently enter the photodetector as noise light, resulting in a decrease in measurement accuracy. Accordingly, proposed as a solution to this problem is an eye refractive power measurement apparatus in which the measurement target is arranged at a decentered position from an optical axis of the objective lens to dissipate the measurement light reflected by the objective lens to be off-axis, preventing the measurement light from entering the photodetector as noise light (see Japanese Patent Application Unexamined Publication No. Hei 4-73038).

Additionally, as for the measurement optical system of the eye refractive power measurement apparatus, in a case where the position of the measurement target is fixed, an image of the measurement target formed on the fundus is clear if the examinee's eye is close to emmetropia; however, if the examinee's eye has a refractive error, the image of the measurement target formed on the fundus becomes blurred and an S/N ratio (signal-to-noise ratio) at the photodetector is lowered to decrease measurement accuracy. In addition, in a case where the position of the photodetector is fixed, not only the image of the measurement target formed on the photodetector becomes blurred, but also its position on the photodetector changes if the examinee's eye has a refractive error; therefore, a resolution is lowered to decrease measurement accuracy if a wide measurement range is to be covered. This problem can be overcome in such a manner that the measurement target and at least one of the photodetector and an image-forming member in the photo-receiving optical system are moved in a direction of their optical axis to have a positional relationship optically conjugate with the fundus.

However, a combination of the configuration that the measurement light reflected by the objective lens is dissipated to be off-axis and the configuration that the measurement target and at least one of the photodetector and the image-forming member are moved in the optical axis direction brings about change in a reflection angle of the measurement light reflected by the objective lens; therefore, it is difficult to prevent noise light from entering the photodetector over a wide measurement range.

SUMMARY OF THE INVENTION

An object of the invention is to overcome the problems described above and to provide an eye refractive power measurement apparatus capable of accurate measurement while preventing noise light from entering a photodetector even in a configuration that a measurement target is moved in a direction of an optical axis.

To achieve the objects and in accordance with the purpose of the present invention, an eye refractive power measurement apparatus has a measurement optical system including a measurement optical axis, a hole mirror having an aperture through which the optical axis passes and a reflective surface around the aperture, a concave mirror arranged on the optical axis, a projection optical system having a measurement target arranged on the optical axis, which projects measurement light from the measurement target onto a fundus of the examinee's eye via the aperture of the hole mirror and the concave mirror and a photo-receiving optical system having an image-forming member and a photodetector which are arranged on the optical axis, which photo-receives the measurement light reflected from the fundus via the concave mirror, the reflective surface of the hole mirror and the image-forming member by using the photodetector, a movement unit which moves the measurement target and at least one of the image-forming member and the photodetector in a direction of the optical axis to have a positional relationship optically conjugate with the fundus, and a calculation part which obtains eye refractive power based on any one of a travel position and a travel amount of at least one of the image-forming member and the photodetector and an output from the photodetector.

In another aspect of the present invention, an eye refractive power measurement apparatus has a measurement optical system including a measurement optical axis, a hole mirror having an aperture through which the optical axis passes and a reflective surface around the aperture, a concave mirror arranged on the optical axis, a projection optical system having a measurement target arranged on the optical axis and movable in a direction of the optical axis, which projects measurement light from the measurement target onto a fundus of the examinee's eye via the aperture of the hole mirror and the concave mirror and a photo-receiving optical system having an image-forming member and a photodetector arranged on the optical axis, at least one of which is movable in the optical axis direction, which photo-receives the measurement light reflected from the fundus via the concave mirror, the reflective surface of the hole mirror and the image-forming member by using the photodetector, and a calculation part which obtains eye refractive power based on any one of a travel position and a travel amount of at least one of the image-forming member and the photodetector which are moved to have a positional relationship optically conjugate with the fundus and an output from the photodetector.

Additional objects and advantages of the invention are set forth in the description which follows, are obvious from the description, or may be learned by practicing the invention. The objects and advantages of the invention may be realized and attained by the eye refractive power measurement apparatus in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

FIGS. 3A and 3B are views for illustrating a method of correcting an astigmatic component associated with the use of a parabolic mirror.

DETAILED DESCRIPTION OF THE PREFERRED EMBODIMENTS

Figure 1:
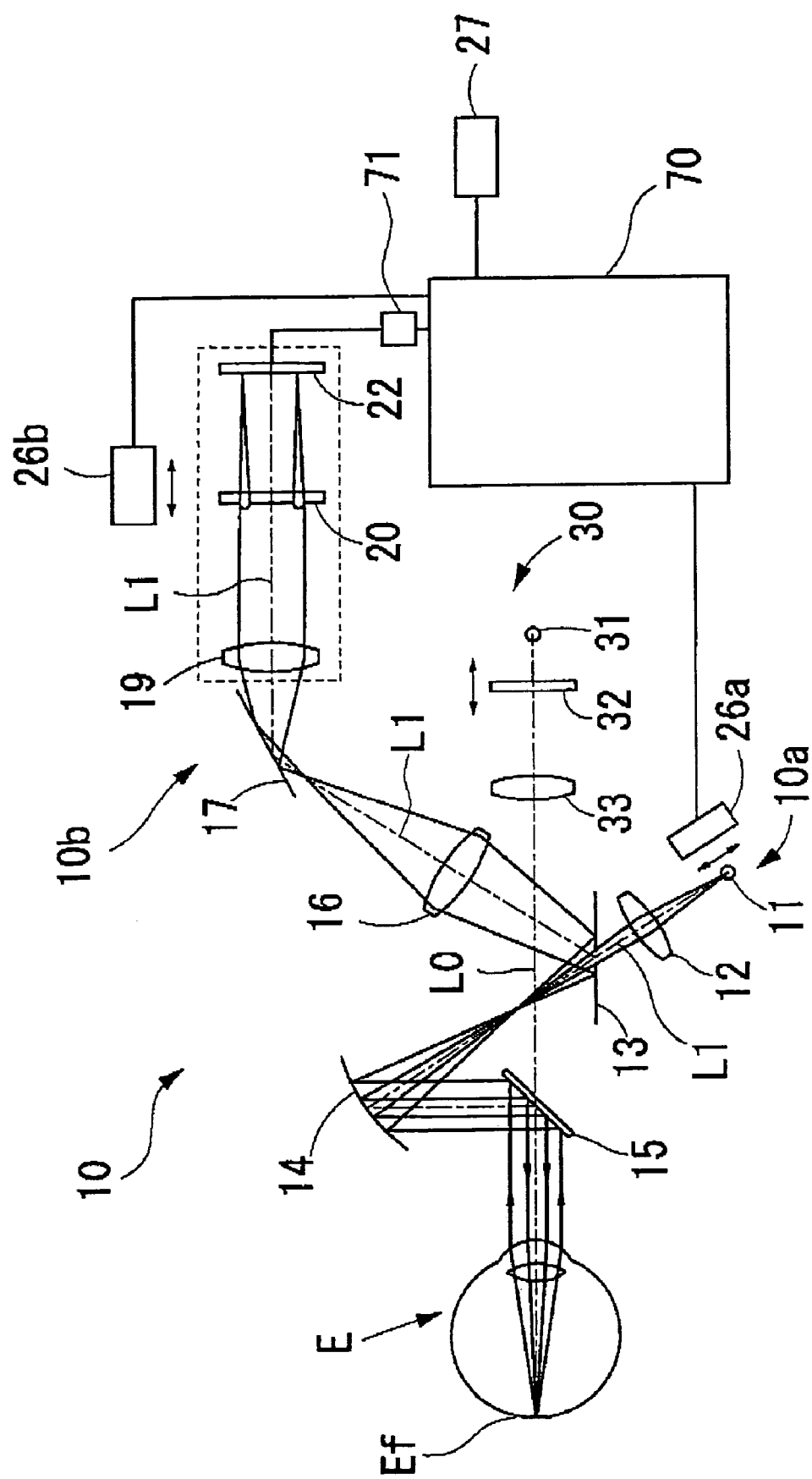
FIG. 1 is a view showing a schematic configuration of an optical system and a control system in an eye refractive power measurement apparatus consistent with one embodiment of the present invention.

A detailed description of one preferred embodiment of an eye refractive power measurement apparatus embodied by the present invention is provided below with reference to the accompanying drawings. FIG. 1 is a view showing a schematic configuration of an optical system and a control system in the eye refractive power measurement apparatus consistent with one embodiment of the present invention.

A measurement optical system 10 includes a projection optical system 10a for projecting spot-shaped measurement light onto a fundus Ef via a central pupillary portion of an eye E of an examinee and a photo-receiving optical system 10b for photo-receiving the measurement light reflected from the fundus Ef via a peripheral pupillary portion of the eye E. The projection optical system 10a includes an infrared point light source 11 such as an LED and an SLD, a relay lens 12, a hole mirror 13, a parabolic mirror 14 being a concave mirror having imaging ability, and a half mirror 15 which are arranged on a measurement optical axis L1. While the light source 11 acts as a measurement target, a measurement target plate having a spot-shaped aperture (opening) may be additionally arranged on the optical axis L1. The hole mirror 13 has an aperture (opening) at the center through which the optical axis L1 passes. The parabolic mirror 14 is an off-axis aspherical mirror, which shifts an optical axis of reflecting light from an optical axis of entering light, and reflects the measurement light relayed by the relay lens 12 to be parallel light with its optical axis shifted. In addition, the parabolic mirror 14 has a property of, when the parallel light to the optical axis enters, converging the parallel light to a certain point while not generating an aberration.

The photo-receiving optical system 10b shares the half mirror 15, the parabolic mirror 14 and the hole mirror 13 with the projection optical system 10a, and includes a relay lens 16 and a total reflection mirror 17 which are arranged on the optical axis L1 in a reflecting direction of the hole mirror 13, and a collimator lens 19, a ring lens 20 and an image-pickup element 22 being a two-dimensional photodetector such as a CCD which are arranged on the optical axis L1 in a reflecting direction of the mirror 17. The image-pickup element 22 is arranged at a back focal point of the ring lens 20. An output from the image-pickup element 22 is inputted to a calculation control part 70 via an image processing part 71.

Figures 2A, 2B:
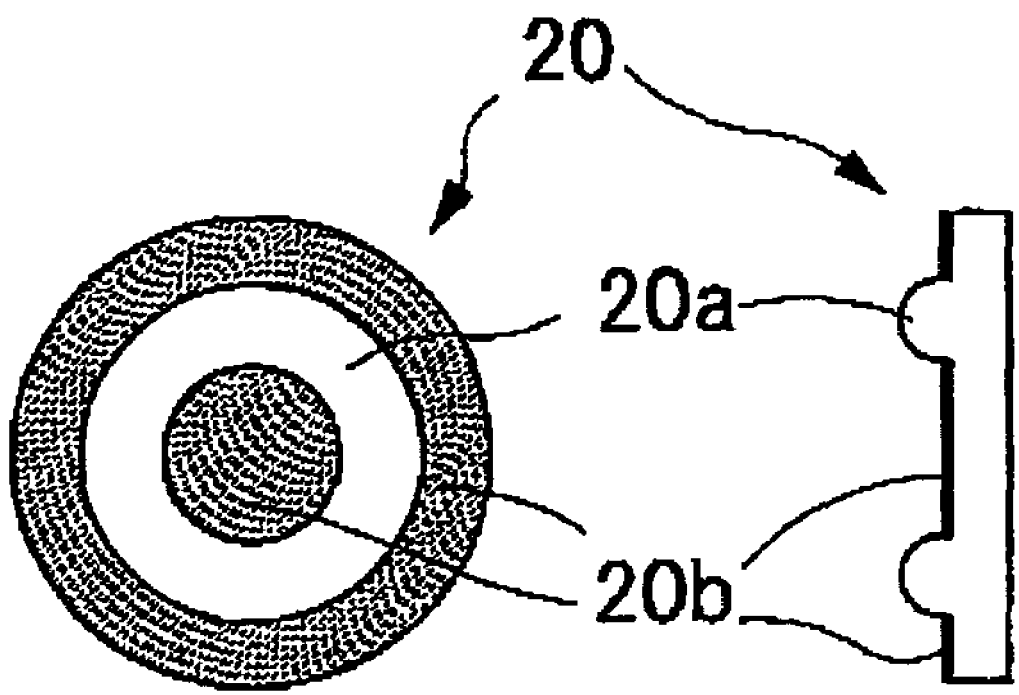
FIGS. 2A and 2B are views showing a schematic configuration of a ring lens.

As shown in FIGS. 2A and 2B, the ring lens 20 is constituted of a lens portion 20a where a cylindrical lens is formed in a ring shape on one side of a transparent plate, and a light shielding portion 20b formed by coating for light shielding which is provided to other portions than the ring-shaped cylindrical lens forming the lens portion 20a. Owing to such a configuration, a ring-shaped aperture (opening) is formed on the ring lens 20. Accordingly, the measurement light reflected from the fundus Ef is, via the peripheral pupillary portion, picked up in a ring shape of a size corresponding to the ring-shaped aperture When approximately parallel light enters the ring lens 20, a ring image of the same size as the ring-shaped aperture is formed on the image-pickup element 22 arranged at the focal point of the ring lens 20. That is to say, the ring lens 20 constitutes an image-forming member which separates the measurement light reflected from the fundus Ef into a ring shape and forms the ring image on the image-pickup element 22 by its light-collecting action. Besides, in the ring lens 20, the ring portion 20a and the light shielding portion 20b may be constituted of separate members.

Incidentally, in the photo-receiving optical system 10b, another configuration may be employed which provides apertures (openings) in at least three meridian directions which are arranged on one circumference having the optical axis L1 at the center, a prism which deflects light passing through the respective apertures to a direction away from the optical axis L1, and a condenser lens, instead of the ring lens 20. In addition, still another configuration may be employed which provides, a lens array with microlenses two-dimensionally arranged on a grid, instead of the ring lens 20 (namely, a configuration of a Hartmann-Shack wavefront sensor).

The light source 11 is arranged movable in a direction of the optical axis L1 by a movement unit 26a consisting of a motor and the like. In addition, the collimator lens 19, the ring lens 20 and the image-pickup element 22 are arranged movable in a direction of the optical axis L1 by a movement unit 26b consisting of a motor and the like. The movement unit 26a and the movement unit 26b move synchronously the light source 11 and the collimator lens 19 to the image-pickup element 22 to have a positional relationship optically conjugate with the fundus Ef. A travel position (travel amount) of these components is detected by a potentiometer 27. Besides, regardless of the movement of these components, the hole mirror 13 and the ring lens 20 are arranged to have a positional relationship optically conjugate with a pupil under a fixed magnification. The movement unit 26a, the movement unit 26b, and the potentiometer 27 are connected to the calculation control part 70. Incidentally, the term "conjugate" referred to in the present specification represents that the positional relationship does not have to be strictly conjugate but may be conjugate only with needed accuracy in relation to measurement accuracy.

The measurement light from the light source 11 is projected onto the fundus Ef through the relay lens 12 to the half mirror 15 to form a light-source image in a spot shape on the fundus Ef. The light of the light-source image formed on the fundus Ef is reflected and scattered thereby to exit from the eye E. Then, the light is reflected by the half mirror 15 and collected by the parabolic mirror 14 to be reflected by a surface around the aperture of the hole mirror 13, and passes through the relay lens 16 and the mirror 17 to be made into approximately parallel light by the collimator lens 19 and made into ring-shaped light by the ring lens 20, and is photo-received on the image-pickup element 22. In the projection optical system 10a, the measurement light which is thin is projected onto the fundus Ef via the central pupillary portion, and in the photo-receiving optical system 10b, the measurement light reflected from the fundus Ef is photo-received (picked up) via the peripheral pupillary portion. The ring-shaped light photo-received (picked up) through the ring lens 20 is, for example, 2.0 mm in inside diameter and 2.8 mm in outside diameter on a pupillary surface.

Here, in a case where the eye E is emmetropia and the image-pickup element 22 is made conjugate with the fundus Ef, the measurement light reflected from the fundus Ef enters the ring lens 20 as approximately parallel light;

therefore, a ring image having the same size and shape as the ring-shaped aperture of the ring lens 20 is formed on the image-pickup element 22. On the other hand, in a case where the eye E has abnormality in a spherical component, a ring image of a size corresponding to an error of the spherical component is formed on the image-pickup element 22. Further, in a case where the eye E has abnormality in an astigmatic (cylindrical) component, an oval ring image corresponding to an error of the astigmatic component is formed on the image-pickup element 22. Accordingly, by analyzing the size and shape of the ring image formed on the image-pickup element 22, a refractive error in each meridian direction may be obtained, to which predetermined processing is provided to obtain values of S (spherical power), C (astigmatic (cylindrical) power) and A (an astigmatic (cylindrical) axial angle). Besides, the size and shape of the ring image may be obtained from an edge position of the ring image, the barycenter position or the peak position of the ring image in light intensity level, and the like.

Further, the light source 11 and the image-pickup element 22 are arranged to have a positional relationship conjugate with the fundus Ef by moving the light source 11, and the collimator lens 19, the ring lens 20 and the image-pickup element 22 in the optical axis L1 direction while making the ring image thinnest, brightest, or making an average size of the ring image the same as the size of the ring-shaped aperture of the ring lens 20. Then, the travel position (travel amount) detected by the potentiometer 27 is converted to the error of the spherical component. A refractive error of the eye E in each meridian direction may be obtained as the sum of this error of the spherical component and the refractive error in the each meridian direction obtained from the ring image on the image-pickup element 22. In this way, by moving the light source 11 in the optical axis L1 direction to have the positional relationship conjugate with the fundus Ef, the light-source image can be clearly formed on the fundus Ef even if the eye E has a great refractive error, and the S/N ratio of the ring image formed on the image-pickup element 22 can be prevented from lowering. Further, by moving the image-pickup element 22 in the optical axis L1 direction to have the positional relationship conjugate with the fundus Ef, the great refractive error can be handled without enlarging an image-pickup surface (photo-receiving surface) of the image-pickup element 22, and a decrease in resolution for analyzation of the ring image can be prevented. Incidentally, the movement of the image-pickup element 22 encompasses not only direct movement of the image-pickup element 22 but also movement of the optical members (image-forming members) from the hole mirror 13 to the collimator lens 19.

A fixation target presenting optical system 30 includes a projection lens 33, a fixation target 32, and a visible light source 31 which are arranged on an optical axis L0 (which is made coaxial with the optical axis L1) in a transmitting direction of the half mirror 15. At the time of eye refractive power measurement the light source 31 and the fixation target 32 are moved in a direction of the optical axis L0 to fog the eye E. Light from the light source 31 illuminates the fixation target 32, and the light therefrom passes through the projection lens 33, and then a part thereof is transmitted through the half mirror 15 to head for the eye E. In this way, the eye E can be fixated on the fixation target 32.

In the apparatus having the configuration as above, when the light source 11 is lit at the time of the eye refractive power measurement, the measurement light from the light source 11 passes through the relay lens 12 and the aperture of the hole mirror 13 to be reflected by the parabolic mirror 14, and a part thereof is reflected by the half mirror 15 to head for the eye E. At this time, since the parabolic mirror 14 has only one reflective surface and all the measurement light reflected by the parabolic mirror 14 heads for the eye E, the measurement light does not enter the image-pickup element 22 as noise light even if the light source 11, and the collimator lens 19, the ring lens 20 and the image-pickup element 22 are moved in the optical axis L1 direction. The measurement is performed in a state where the eye E is fixated on the fixation target 32 and fogged, and the light source 11 and the image-pickup element 22 are moved to have the positional relationship conjugate with the fundus Ef. As mentioned above, the calculation control part 70 calculates a refractive value including astigmatism based on the travel position (travel amount) of the image-pickup element 22 and an analysis result of the corresponding ring image formed on the image-pickup element 22.

Meanwhile, in association with the use of the aforementioned parabolic mirror 14 being an off-axis aspherical mirror, an aberration is generated in the reflecting light from the off-axis aspherical mirror and appears as an astigmatic component if the entering light is not parallel light; therefore, it is preferable to previously correct the aberration. Hereinafter, this correction will be described referring to FIGS. 3A and 3B.

As the parabolic mirror 14 (in solid lines), an off-axis part of a parabolic mirror 140 (in dotted lines) is used. Here, a plane direction including a principal ray and the optical axis is referred to as a meridional-plane direction, and a direction normal to the meridional-plane direction is referred to as a sagittal-plane direction. Incidentally, in this embodiment, a portrait orientation of the paper providing FIG. 1 and the meridional-plane direction in FIGS. 3A and 3B represent the same direction. In a case where the parallel light enters the parabolic mirror 14, the reflecting light in the meridional-plane direction and the reflecting light in the sagittal-plane direction converge at a convergent point A on the optical axis L1 as shown in FIG. 3A. Contrary to the case where the parallel light enters, in a case where convergent light or diffused light enters the parabolic mirror 14, the reflecting light in the meridional-plane direction and the reflecting light in the sagittal-plane direction converge at different points on the optical axis L1 as shown in FIG. 3B. In other words, a convergent point C of the reflecting light in the meridional-plane direction is located at a farther position on the optical axis L1 than a convergent point B of the reflecting light in the sagittal-plane direction. In this case, even if the refractive error of the examinee's eye includes only a spherical component, the ring image formed on the image-pickup element 22 becomes oval. For example, when the image-pickup element 22 is moved until the convergent point B of the reflecting light in the sagittal-plane direction and the image-pickup element 22 have a positional relationship optically conjugate with each other, the ring image on the image-pickup element 22 becomes oval, having the major axis in the meridional-plane direction, thereby causing, if an analysis is made as it is, the spherical component to appear as an astigmatic component. Therefore, an analysis is to be conducted on a shape of the ring image at the time when a convergent point of the reflecting light in the sagittal-plane direction and the image-pickup element 22 become conjugate to previously prepare data for correcting the astigmatic component in each meridian direction in relation to a travel position of the image-pickup element 22 at the time. The correction data is previously stored in a storage part in the calculation control part 70. At the time of the measurement, the refractive error in the sagittal-plane direction is obtained from the travel position of the image-pickup element 22 at the time when the convergent point of the reflecting light in the sagittal-plane direction and the image-pickup element 22 become conjugate, and refractive power in other meridional directions is obtained while subjected to corrections based on the correction data for the astigmatic component. As a result, more accurate measurement can be performed.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated It is intended that the scope of the invention be defined by the claims appended hereto, and their equivalents.

What is claimed is:

1. An eye refractive power measurement apparatus for measuring eye refractive power of an eye of an examinee, the apparatus comprising:
    a measurement optical system including
        a measurement optical axis,
        a hole mirror having an aperture through which the optical axis passes and a reflective surface around the aperture,
        a concave mirror arranged on the optical axis,
        a projection optical system having a measurement target arranged on the optical axis, which projects measurement light from the measurement target onto a fundus of the examinee's eye via the aperture of the hole mirror and the concave mirror, and
        a photo-receiving optical system having an image-forming member and a photodetector arranged on the optical axis, which photo-receives the measurement light reflected from the fundus via the concave mirror, the reflective surface of the hole mirror and the image-forming member by using the photodetector;
    a movement unit which moves the measurement target and at least one of the image-forming member and the photodetector in a direction of the optical axis to have a positional relationship optically conjugate with the fundus; and
    a calculation part which obtains eye refractive power based on: any one of a travel position and a travel amount of at least one of the image-forming member and the photodetector; and an output from the photodetector.

2. The eye refractive power measurement apparatus according to claim 1, wherein the concave mirror includes an off-axis aspherical mirror.

3. The eye refractive power measurement apparatus according to claim 2, wherein the calculation part corrects an astigmatic component, which is generated when the measurement light reflected from the fundus is reflected by the concave mirror, based on any one of the travel position and the travel amount when moving at least one of the image-forming member and the photodetector to have the positional relationship conjugate with the fundus.

4. An eye refractive power measurement apparatus for measuring eye refractive power of an eye of an examinee, the apparatus comprising:
    a measurement optical system including
        a measurement optical axis,
        a hole mirror having an aperture through which the optical axis passes and a reflective surface around the aperture,
        a concave mirror arranged on the optical axis,
        a projection optical system having a measurement target arranged on the optical axis and movable in a direction of the optical axis, which projects measurement light from the measurement target onto a fundus of the examinee's eye via the aperture of the hole mirror and the concave mirror, and
        a photo-receiving optical system having an image-forming member and a photodetector arranged on the optical axis, at least one of which is movable in the optical axis direction, which photo-receives the measurement light reflected from the fundus via the concave mirror, the reflective surface of the hole mirror and the image-forming member by using the photodetector; and
    a calculation part which obtains eye refractive power based on: any one of a travel position and a travel amount of at least one of the image-forming member and the photodetector which are moved to have a positional relationship optically conjugate with the fundus; and an output from the photodetector.

5. The eye refractive power measurement apparatus according to claim 4, wherein the concave mirror includes an off-axis aspherical mirror.

6. The eye refractive power measurement apparatus according to claim 5, wherein the calculation part corrects an astigmatic component, which is generated when the measurement light reflected from the fundus is reflected by the concave mirror, based on any one of the travel position and the travel amount when moving at least one of the image-forming member and the photodetector to have the positional relationship conjugate with the fundus.

* * * * *